United States Patent [19]

Velez et al.

[11] Patent Number: 4,852,988
[45] Date of Patent: Aug. 1, 1989

[54] VISOR AND CAMERA PROVIDING A PARALLAX-FREE FIELD-OF-VIEW IMAGE FOR A HEAD-MOUNTED EYE MOVEMENT MEASUREMENT SYSTEM

[75] Inventors: Jose Velez, Newton; Joshua D. Borah, Mansfield, both of Mass.

[73] Assignee: Applied Science Laboratories, Waltham, Mass.

[21] Appl. No.: 243,330

[22] Filed: Sep. 12, 1988

[51] Int. Cl.$^4$ .............................................. A61B 3/14
[52] U.S. Cl. .................................. 351/210; 351/209; 351/158
[58] Field of Search ...................... 351/209, 210, 158; 350/169, 174

[56] References Cited

U.S. PATENT DOCUMENTS

| | | | |
|---|---|---|---|
| 3,473,868 | 10/1969 | Young et al. | 351/209 |
| 3,507,988 | 4/1970 | Holmes | 178/6.8 |
| 3,542,457 | 11/1970 | Balding et al. | 351/209 |
| 3,583,794 | 6/1971 | Newman | 351/209 |
| 3,594,072 | 7/1971 | Feather et al. | 351/38 |
| 3,623,799 | 11/1971 | Millodot | 351/32 |
| 3,679,295 | 7/1972 | Newman et al. | 351/210 |
| 3,689,135 | 9/1972 | Young et al. | 351/210 |
| 3,984,156 | 10/1976 | Jernigan | 351/210 |
| 4,034,401 | 7/1977 | Mann | 358/93 |
| 4,075,657 | 2/1978 | Weinblatt | 358/93 |
| 4,755,045 | 7/1988 | Borah et al. | 351/210 |
| 4,761,056 | 8/1988 | Evans et al. | 350/174 |

FOREIGN PATENT DOCUMENTS

0125808 11/1984 European Pat. Off. .
0157973 10/1985 European Pat. Off. .

OTHER PUBLICATIONS

Eye-Movement Measurement Techniques by Young and Sheena; from American Psychologist Magazine, Mar. 1975, pp. 315–330.
Methods & Designs Survey of Eye Movement Recording Methods by Young & Sheena; from Behavior Research Methods & Instrumentation, 1975, vol. 7(5), pp. 397–429.
Excerpt from Applied Science Laboratories' Eye-Trac Catalog, 1982, pp. 1–31.
Compensation for Some Second Order Effects to Improve Eye Position Measurements by Sheena & Borah; from Eye Movements-Cognition and Visual Perceptions, 1981, pp. 257–268.
Copy of U.S. Serial No. 848,154 filed 4-4-86 and now abandoned.

Primary Examiner—Rodney B. Bovernick
Assistant Examiner—P. M. Dzierzynski
Attorney, Agent, or Firm—Body, Vickers & Daniels

[57] ABSTRACT

A head-mounted, eye-movement, measurement system is provided with an optically flat glass laminated visor through which the observer views the external scene. Mounted so as to be vertically spaced from one side of the eye's optic axis is an eye tracker module for recording the observer's eye-movement relative to the head, principally by measuring the position of the pupil and corneal reflex, by reflecting near infrared light to and from the observer's eye vis-a-vis the front surface of the visor. Mounted so as to be vertically spaced on the opposite side of the eye's optic axis is a field-of-view camera which records the external scene viewed by the observer by reflecting external scene light from the back side of the visor. The distances and angular relationship of the visor, camera and eye are controlled to eliminate parallax from the field-of-view camera while also providing a stable arrangement permitting wide-angle scene viewing and accurate recordal of eye movements.

57 Claims, 4 Drawing Sheets

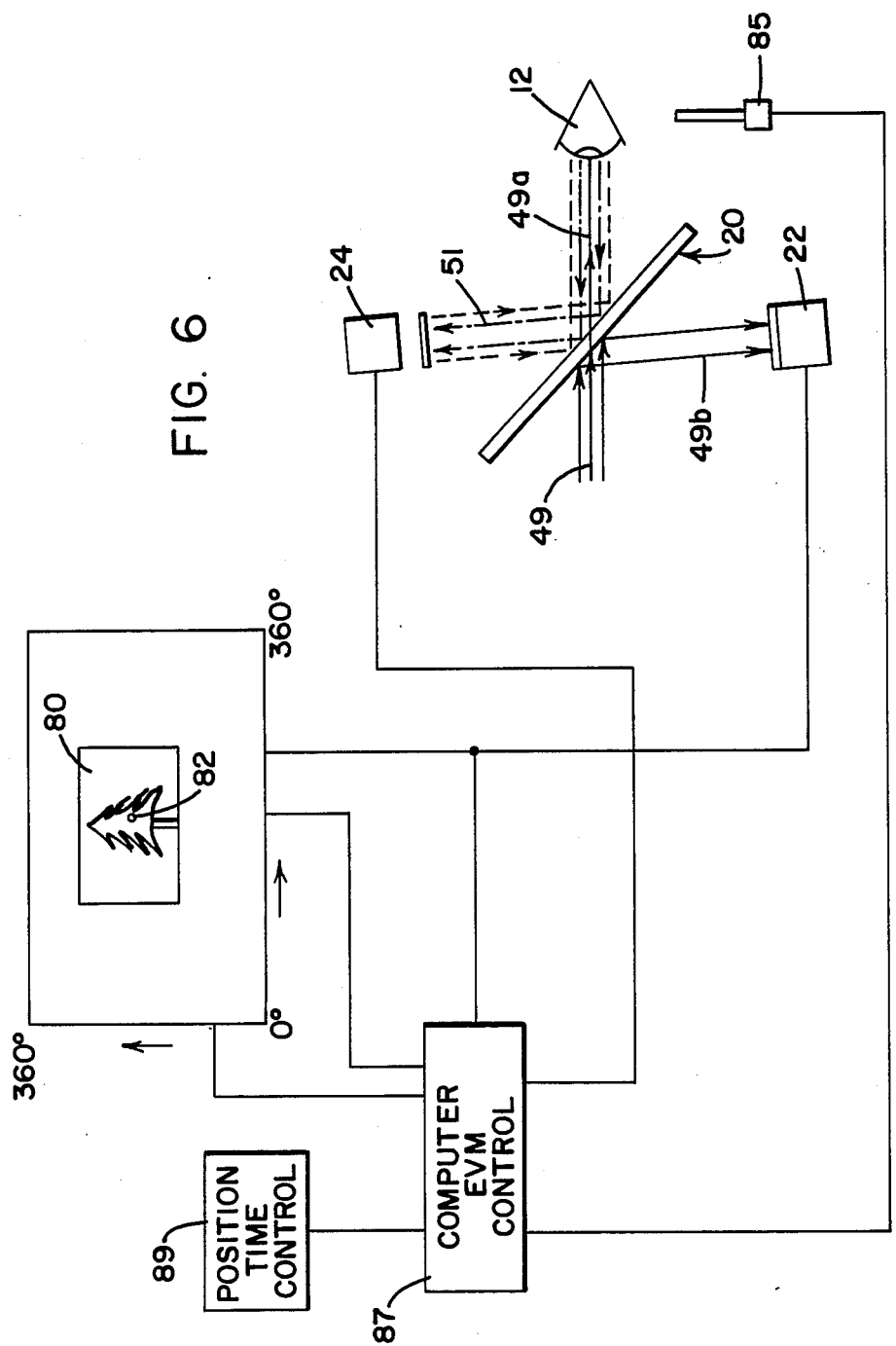

VISOR AND CAMERA PROVIDING A PARALLAX-FREE FIELD-OF-VIEW IMAGE FOR A HEAD-MOUNTED EYE MOVEMENT MEASUREMENT SYSTEM

This invention relates generally to an eye-movement measurement system and more particularly to eye monitoring systems adapted to be mounted to the observer's head.

The invention is particularly applicable to an eye-movement measurement system which utilizes an eye tracker in combination with a point-of-view camera to determine the observer's point of gaze and will be described with particular reference thereto. However, it will be appreciated by those skilled in the art that the invention may have broader application and may be applied in any situation where a picture, preferably a video recording, of the external scene actually viewed by the observer is desired. Additionally, it will be appreciated by those skilled in the art that while the invention has particular application to a headmounted system, the arrangement disclosed can easily be adapted for use in a floor mounted or remote eye-movement measurement system.

INCORPORATION BY REFERENCE

The following documents are incorporated herein by reference as background material and form a part hereof:

(1) An article entitled "Eye-Movement Measurement Techniques" by L. R. Young & David Sheena appearing in *American Psychologist*, Volume 30, No. 3, dated March 1975, Pages 315–330;

(2) Methods & Design - Survey of Eye Movement Recording Methods" by Young & Sheena, Behavior Research Methods & Instrumentation, 1975, Vol. 7 (5), Pages 397–429;

(3) "Eye-Trac" Catalog by Applied Science Laboratories, copyright 1982, pages 1–31;

(4) U.S. Pat. No. 4,034,401 to Mann;

(5) U.S. Pat. No. 3,542,457 to Balding et al;

(6) European Patent Application Publication No. 0-125-808 dated Nov. 21, 1984;

(7) European Patent Application Publication No. 0-157-973 dated Nov. 16, 1985;

(8) U.S. Pat. No. 4,755,045 by the present inventors; and (9) U.S. Ser. No. 848,154, filed Apr. 4, 1986 and assigned to Applied Science Laboratories.

BACKGROUND

There are a large number of eye-movement measuring techniques in the art and the principal ones are disclosed in the Young & Sheena articles which are incorporated by reference herein. This invention relates to those eyemovement measuring techniques which use an external light source, generally at near infrared wavelength, which is reflected from some portion of the eye to obtain a measurement of eye position or fixation. Generally, such techniques are classified as corneal reflection per se, corneal reflection-pupil center, corneal reflection-double Purkinje image, pupil tracking per se, limbus (i.e., the boundary between the iris and the sclera) tracking, eyelid tracking and combinations thereof. When used throughout this specification, reference to "eye tracker" or "eye tracker means" or "eye tracker mechanism" means any and all conventional mechanisms which utilize any of the aforementioned tracking techniques principally be measuring reflection of light from or over a portion of the eye. This is in distinction to electrooculography and contact lens eye-movement measurement techniques which do not fall within the definition of an eye tracker as used herein.

Eye trackers of the type to which this invention relates, may be further classified as (i) head-mounted, in the sense that the principal measurement instruments are secured by a helmet or head band to the observer's head or (ii) "remote" or floor mounted in the sense that no instruments are applied to the observer's head even though chin rests or other devices might be used to immobilize the observer's head movement of (iii) a combination of "head-mounted" and "remote" or "hybrid" devices which do not exist in a practical, commercial sense, but are present in any theoretical consideration.

A totally "remote" eye tracker system is produced by Applied Science Laboratories, the assignee of the present invention, in its 1996 and 1998 model lines which are further described in our U.S. Pat. No. 4,755,045, U.S. patent application Ser. No. 848,154, and in ASL's Eye Trac Catalog, all incorporated by reference herein. In the 1998 model, the position of a servo controlled tracking mirror is controlled to maintain the eye image within the eye camera field-of-view so that eye line-of-gaze can be determined with the pupil center to corneal reflection technique. In this manner, rapid, unrestrained movements of the head will not result in loss of eye measurement even with as much as one foot of lateral or vertical head motion. Because there are no head-mounted instruments nor any other distracting instrumentation present to the observer, the 1996 and 1998 systems are ideal for eye tracking measurements where the observer is seated, such as in the cockpit of a flight trainer or in a chair watching video commercials, etc. However, there are countless research, industrial and military applications where it is desired to accurately see what a person is looking at instead of projecting a predetermined scene and monitoring the reaction of the observer to the projected scene. Such applications typically use headmounted systems to monitor eye-movements.

As noted, hybrid head-mounted - remote systems exist in the literature. For example, in EPC application No. 0157973, the external light source for directing the near infrared light for eye measurement purposes is mounted in the observation room while the corneal reflection instrument is attached to eyeglass frames affixed to the observer, who is viewing a scene projected on a screen. In U.S. Pat. No. 4,034,401, both the near infrared light source and the eye tracker camera (which is of the limbus tracking type) are reflected off a pilot's helmet to locate the eye position relative to an externally generated weapons pointing display reflected on the windshield of the aircraft. In both applications, the observer is seated or stationary and looking at a scene which is projected in front of him. To partially mount some of the eye tracker mechanism to the head of the observer simply encumbers the observer without presenting any enhancement of the system when compared with the ASL 1998 model used either in an airplane cockpit environment or in a seated environment for viewing artificially projected scenes such as commercials and the like. For such reasons, "hybrid" eye measurement systems are not commercially practical.

This then leaves head-mounted systems to satisfy those applications, i.e., observer movement and/or real life scene viewing, which cannot be addressed by head-free systems. A head-mounted, eye monitoring system as thus defined herein requires a field-of-view or scene camera which records any external scene as actually viewed by the observer and an eye tracker mechanism, both items secured by an appropriate head band or helmet to the head of the observer. Different, head-mounted systems have been developed in the art for different eye measuring techniques, principally limbus tracking and corneal reflection.

One typical limbus tracking arrangement uses eyeglasses with an infrared source of illumination mounted at the bottom of the lens and flanked on either side by photo cells which electrically record the light reflected to generate an eye image. A field-of-view camera is then added to the eyeglasses to obtain a point-of-gaze display. Examples of such head-mounted limbus tracking systems may be found in ASL's Eye Trac Catalog and in several embodiments disclosed in European Patent Application No. 0,125,808, which also discloses use of CCD chips for imaging. As noted by Young & Sheena, the eyeglass limbus tracking arrangement is suitable for some applications, but is limited with respect to vertical eye-movement measurement. Also, the field-of-view camera is mounted on one side of the eyeglass frame while the eye position measurement instruments are located on the other side and this side-by-side mounting arrangement introduces a parallax error, which may or may not present a problem.

To obtain more precise eye measurement over both horizontal and vertical eye-movement, corneal reflex cameras have been used in head-mounted eye monitoring systems which also employ field-of-view cameras to obtain point of gaze information from an observer having freedom of movement. As disclosed in the Young & Sheena articles, early head-mounted corneal reflex eye monitoring systems used a periscope arrangement with the bottom of the scope carrying the infrared light source and scope lenses which reflected the infrared image to the top of the scope. The top of the scope was mounted on top of the observers head and carried the scene lens and an eye tracker camera in combination with a beam splitter prism for superimposing the corneal reflection as a spot of light onto the scene recorded from the field-of-view camera. Because of difficulties encountered in maintaining the infrared light source appropriately centered relative to the cornea, this concept has been modified into a side-by-side arrangement where the field-of-view camera is mounted on one side of the observer's head while the eye tracker mechanism with appropriate optics is mounted on the opposite side. Fiber optics have been used to lighten the helmet weight. One example of such an arrangement is disclosed in U.S. Pat. No. 3,542,457, incorporated by reference herein. As best illustrated in U.S. Pat. No. 3,542,457, a dichroic fixed mirror is used to reflect light from an infrared lamp to the eye spot or eye track camera for subsequent superimposition on the scene viewed by the field-of-view camera, the eye also viewing the scene through the dichroic mirror which is transparent to visible light. As in the earlier periscope version of the helmet, U.S. Pat. No. 3,542,457 uses a complicated optic system to reflect the light to the cornea and back to the eye tracker camera.

It should also be noted that in the literature, specifically for one of the embodiments disclosed in EPA No. 125-808-A, the concept of using an eye tracker camera on the "limbus tracking" eyeglass frame for recording corneal reflection without complicated optics is used. However, that disclosure fixed the infrared lamp to the bridge of the eyeglass frame and would be suspect to the errors and inaccuracies of the earlier corneal reflex head-mounted systems which used a light source simply positioned in front of the eye.

In addition, it is known and disclosed in ASL's Eye Trac Catalog and discussed in some length by Young & Sheena that any number of different sensors, i.e., magnetic head, optic, mechanical, etc., may be applied to the observer's head to measure the orientation of the eye in space to obtain the point-of-gaze (the angle of gaze relative to a reference point in the visual field) relative to ground.

In summary, the limbus tracking eyeglasses are limited in their ability to measure eye-movement and the helmet mounted corneal reflection cameras require optics which somewhat tend to distort the spot image projection and require extensive calibration and readjustment. More importantly, all head-mounted, eye-movement measurement systems heretofore mounted the field-of-view or scene camera short distance from the eye (or eyes) whose movement was being recorded in a manner which introduced a perspective or parallax error. The parallax error could allow the field-of-view camera to see an object which is actually hidden and thus not visible to the observer. This difference in field-of-view is significantly noticeable at short distances and somewhat insignificant at infinity. When an eye tracker is used with the field-of-view camera in a head-mounted system, the system must be calibrated to the scene distance viewed if accurate point-of-gaze data is to be obtained. That is the field-of-view scene recorded must be adjusted for parallax for the distance of the particular viewed scene and the eye tracker than adjusted relative to the adjusted field-of-view scene thus recorded if accurate point-of-gaze information in space which is depended on absolute eye position, is to be obtained. Heretofore, mechanical and/or optical conflicts have either resulted in camera incompatibility with a head-mounted eye tracker or limitations of eye tracker performance to a specifically calibrated distance.

SUMMARY OF THE INVENTION

Accordingly, it is one of the principal objects of the present invention to provide a head-mounted eye-movement monitoring system which provides accurate recording of the observer's eye-movement relative to the external scene as actually viewed by the observer.

This feature, along with other features of the invention, is achieved in a head-mounted eye-movement system which monitors an observer's view of any external scene as seen through at least one of the observer's eyes. The system includes a field-of-view camera positioned vertically on one side of the optic axis of the eye for recording the scene. An eye tracker mechanism which includes an eye tracking source of near infrared light for recording the position of the eye as the observer views the scene is vertically positioned on the opposite side of the eye's optic axis. A visor is vertically positioned at an angle between the field-of-view camera and the eye tracker mechanism at the intersection of the eye's optic axis with the field-of-view camera's optic axis. The visor is transparent to visible light to permit the observer to view the external scene while looking through the visor. An optical coating arrangement is provided on the visor which reflects the near infrared eye tracker light from the eye of the observer to actuate the eye tracker mechanism in accordance with standard practice while simultaneously reflecting light from the external scene to the field-of-view camera for recording the external scene viewed by the observer. The two way, oppositely directed, reflective reverse mirror views of the visor (actually a three way utilization) permits a stable, vertical mount arrangement with all measuring instrumentation positioned over or under the eye whose movement is to be recorded. Thus the system can be easily modified to include a second field-of-view camera for the other eye in combination with an additional eye tracker mechanism so that the movement of both eyes can be easily recorded. In such an arrangement the visor would simply be laterally extended across the face of the observer. In addition, when the eye tracker mechanism utilized any of the corneal reflection techniques, the general arrangement described permits a very simple optic system, essentially comprising only the visor, to reflect a coaxial infrared light source to the eye and back to the eye tracker camera avoiding the intricacies of the prior art helmet mounted optics and inherently resulting in a clearer eye tracker picture which maintains proper eye alignment irrespective of eye-movement.

In accordance with another principal feature of the invention, a helmet or head band arrangement is provided which precisely mounts the field-of-view camera in a fixed relationship to the eye of the observer. More particularly, adjustment mechanisms associated with the visor, field-of-view camera and the helmet space the visor at equal distances between the eye and the field-of-view camera. This distance is measured from the intersection point of the eye's optic axis with the field-of-view camera's optic axis. Importantly, the attitude or plane of inclination of the visor is adjusted so that the angle between the visor and the field-of-view camera axis is equal to the angle between the visor and the eye's optic axis, both angles being measured from the same side of the visor. This geometric relationship minimizes or eliminates parallax and permits the field-of-view camera to accurately record the external scene as visualized or as actually seen through the observer's eye. In concept, the use of the visor which is at least partially transparent to visible light to the observer's eye so that the observer can view the external scene while also partially reflective of the external light to a field-of-view camera where the relationship between the eye, visor and field-of-camera is such to minimize, if not totally eliminate, parallax is a feature of the invention which has utility or usefulness in eye studies with or without an eye tracker camera. When this feature of the invention is used in combination with an eye tracker camera using the corneal reflection technique, the optic axis of the eye tracker camera is preferably parallel to that of the field-of-view camera's optic axis so that an accurate and precise positioning and reflection of the near infrared eye tracker camera light source occurs without the position inaccuracies associated either with the mount or the optic adjustments which afflicted the prior art systems.

In accordance with another feature of the invention, the visor is a flat glass laminate having an infrared reflective coating positioned on one side of a glass substrate while a polycarbonate substrate is positioned on the opposite side of the glass substrate by means of an adhesive. The visor, as thus defined, uses an infrared coating which is a conventional or dichroic or "heat mirror". In the head-mounted eye-monitoring system of the present invention, the outer surface of the infrared reflective coating reflects the eye tracker's infrared source light while the opposite surface of the infrared coating reflects the near infrared light transmitted from the external scene to a monochromatic (IR) field-of-view camera. In accordance with the present invention, the conventional type heat mirror thus described is easily modified by mounting a polarizing film on the back surface of the polycarbonate substrate by means of removable clips secured to the ends of the visor. A metallic reflecting film or coating is applied to the opposite side of the polarizing film and a thin non-detrimental air space exists between the polarized layer and the polycarbonate substrate. As thus modified, visible light from the scene is partially reflected by the metallic reflecting film or coating on the polarized film to the field-of-view camera which is now a color (or monochromatic black and white) camera. An infrared cut filter and a polaroid filter is fitted over the lens of the field-of-view camera. In this manner, distinct, conventional video pictures can be obtained on which can be superimposed the eye tracker spot representative of the observer's point of gaze. Importantly, the clips permit the infrared visor to be easily converted to a visible light visor and vice versa. The visor laminates described have minimal thickness of approximately 3 mm for the infrared light visor and approximately 4.5 mm for the visible light visor. As thus constructed, both visors have minimal coloration and visual distortion.

In accordance with other features of the invention, miniaturized imaging sensors such as a charge-coupled semiconductor device (CCD Chip Camera) are employed or alternatively a vidicon tube with optic fiber connections may be employed to permit a rigid, lightweight easily mounted and adjustable head band or helmet for the observer. In addition, any of the conventional head sensing devices can be attached to the helmet to locate the position of the head relative to space or ground which data can then be combined with the eye tracker data locating the position of the eye relative to the head to locate the position of the eye in space or, in effect, relative to the world, throughout a 360° field-of-view.

In accordance with yet another feature of the invention, the visor is dimensionally sized to easily span the observer's face in an unobtrusive manner while permitting maximum eye measurement movement. Significantly, the visor is sized to permit a relatively large field-of-view or scene range of typically 55° horizontal×45° vertical, and this range can be adjustably biased in a vertical direction if required because of the particular scene application being studied.

It is thus an object of the invention to provide a head-mounted eye-movement measurement system which accurately records the field-of-view seen by the observer by correcting or minimizing parallax.

It is another object of the invention to provide a head-mounted eye-movement measurement system which uses instruments vertically mounted relative to the face of the observer to produce a simple optic system.

Another object of the invention is to utilize a flat, glass visor laminate in a head-mounted, eye-movement monitoring system which has minimal visual distortion and coloration artifacts.

Another object of the invention is to utilize a flat reflective-transparent visor in a head-mounted eye monitoring system which produces a vertically adjustable, large or wide field-of-view for tracking point of gaze information.

Still another object of the present invention is to provide a head-mounted, eye-movement measurement system which uses visible light for recording field-of-view images.

Still yet another object of the invention is to provide in a head-mounted, eye-movement monitoring system a visor configuration which reflects near infrared wave light from two different directions or near infrared wave light from one direction and visible light in the opposite direction.

Still yet another object of the invention is to provide an improved head-mounted eye monitoring system which utilizes a two way light reflecting visor to produce a small size, lightweight head-mounted arrangement.

Still yet a more detailed object of the invention is to provide a visor which can be easily converted from a device used to reflect scene light to an infrared field-of-view camera to a device used to reflect visible scene light to a field-of-view camera.

Another general object of the invention is to provide a reflective, transparent visor having any of the aforementioned characteristics for use with any eye-movement measurement system which may be remote and not head-mounted.

Still yet another object of the invention is to provide an improved head-mounted, eye-movement, measurement system which utilized a visor and a particular geometric configuration therewith which permits a side variety of eye tracking mechanisms using different eye-movement measuring techniques to be employed therewith.

Still another object of the invention is to provide an improved head-mounted, eye monitoring system which is relative simple and inexpensive.

These and other objects of the present invention will become apparent to those skilled in the art upon a reading and understanding of the specifications.

DESCRIPTION OF THE DRAWINGS

The invention may take physical form in certain parts and arrangements of parts, a preferred embodiment of which will be described in detail and illustrated in the accompanying drawings which form a part thereof and wherein:

FIG. 6 is a general schematic illustration of the invention illustrating the optics and an absolute view obtained with respect to the invention.

DETAILED DESCRIPTION OF THE INVENTION

Figure 1:
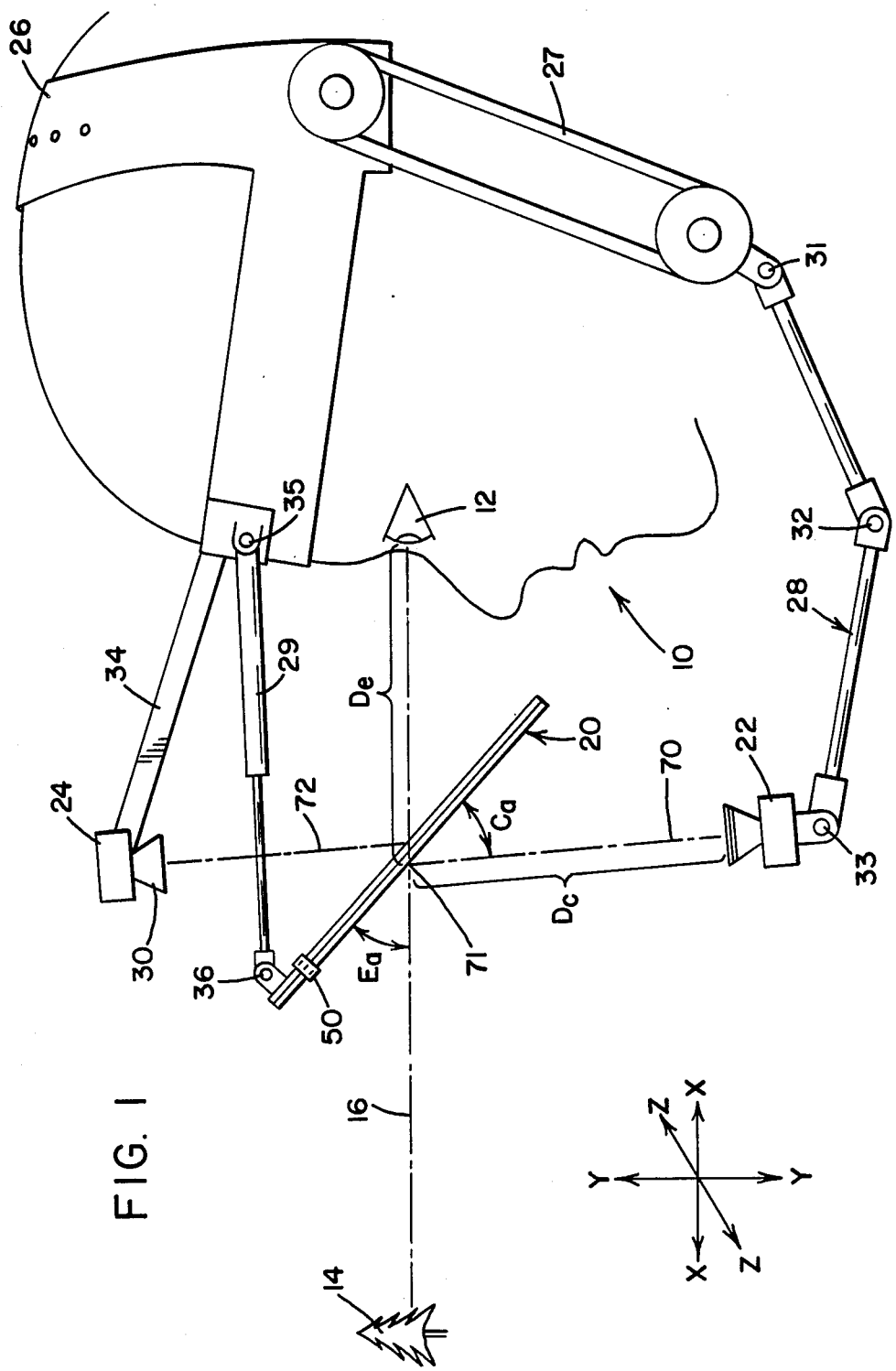
FIG. 1 is a schematic elevation view of the system of the present invention.

Referring now to the drawings wherein the showing are for the purpose of illustrating a preferred embodiment of the invention only and not for the purpose of limiting the same, there is shown a general arrangement in FIG. 1 where an observer 10 is focusing eye 12 on an external scene 14. The optic axis 16 of eye 12 is shown as a dot-dash line in FIG. 1 and observer 10's line of gaze for viewing external scene 14 is directed through a flat laminated visor 20. Visor 20 is a laminated glass which extends laterally in the z-z direction across the face of observer 10 and will be discussed in detail hereafter. Laminated visor 20 is one element of a head-mounted, eye-movement measurement system. The other components of the system include a field-of-view camera 22, an eye-tracker module 24 an a helmet or head band 26 for mounting and adjusting the various positions of visor 20, field-of-view camera 22 and eye tracker module 24 relative to the observer's eye 12. A variety of helmet or head band arrangements 26 exist in the prior art and any particular design or configuration of helmet or head band 26 is believed readily obvious to those skilled in the art and is thus not shown or described in detail herein. What is important is that a helmet or head band 26 contain any number of conventional adjustment mechanisms to permit the proper orientation and placement of field-of-view camera 22, visor 20 and eye tracker module 24 in a manner to be set forth in detail hereafter.

More specifically, FIG. 1 shows a head-mounted system in an x-y plane and a third dimensional z-z axis is defined as a line projecting into or out of the plane of the paper.

Generally, field-of view camera 22 is mounted in an adjustable, swivelable manner to an articulated arm 28 which in turn is mounted to head band 26 by means of a lockable mounting arm 27. The particular articulated arm 28 shown is pivotally pinned at three joints, 31, 32, 33, to permit articulated arm 28 to bend and twist three-dimensionally in a non-telescoping manner and thus properly position field-of-view camera 22 at any desired point in space. Eye-tracker optics module 24 is mounted as a unit to headband 24 and slides in a z-z direction on a dovetailed track (not shown). For drawing position and illustration purposes only, eye-tracker optics module 24 is shown mounted to a fixed arm 34. In practice, a conventional eye-tracker module 24 is simply mounted to headband 26 in a z-z movable direction and contains the necessary position elements or optics to adjust the eye-tracker camera 20 within the module in a conventional manner. A pair of telescoping visor arms 29 (only one is shown) spaced apart from one another in the z-z direction, is pivotally mounted at one end 35 to the helmet or headband 26 and pivotally mounted at the other end 36 to visor 20. This arrangement permits easy adjustment of the distance of visor 20 from observer's eye 12 as well as the angle of visor 20 relative to eye optic axis 16.

Preferably, field-of-view camera 22 is positioned vertically below observer's eye 12 while eye-tracker optics module 24 is positioned vertically above observer's eye 12. The positions, however, can be reversed. Also, the invention will be described with reference to monitoring the position of one eye 12 of observer 10. In such an application, visor 20 need not extend across the face of observer 10. When both eyes of observer 10 are to be monitored, visor 20 must extend across the face of observer 10. Also, a second field-of-view camera 22 mounted on a second articulated arm 18 is positioned on the opposite side of headband 26 and a second eye tracker module 24 must be similarly applied to helmet or head band 26.

As noted above and as diagrammatically indicated in FIG. 6, light from external scene 14 is viewed by observer's eye 12 through visor 20 which is transparent to visible light. Additionally, light form external scene 24 is reflected by visor 20 into field-of-view camera 22. Also, light for eye tracking purposes from the observer's eye 12 is reflected by visor 20 into eye tracker module 24.

Figure 5:
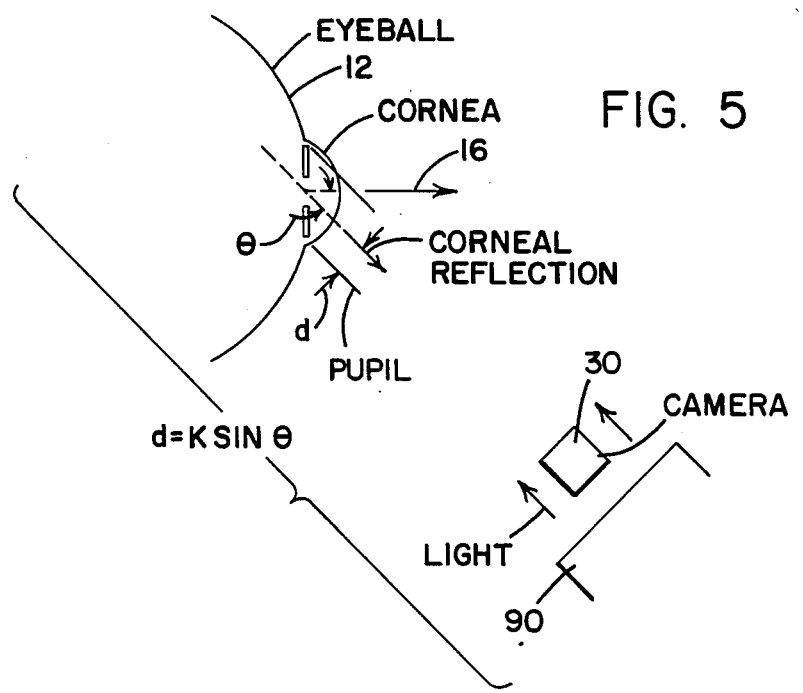
FIG. 5 is a general schematic broadly illustrating measurement with the pupil center to corneal reflection technique.

Eye tracker module 24 can be any conventional eye tracking mechanism used in the art to record eye-movement and can employ any of the measurement techniques discussed above. It is, however, preferred that eye tracker module 24 used in the invention be of the type which measures eyemovement by the pupil center to corneal reflection technique which is generally illustrated in FIG. 5. The reader is referred to FIG. 28 of Young & Sheena's survey article (incorporated herein by reference) for a more definitive explanation than that presented herein. Briefly, a light source 90 in eye tracker module 24 generates a generally infrared beam coaxial with the optic axis of an eye tracker camera 30 in eye tracker module 24. Light source 90 is directed against the cornea of observer's eye 12. Because the cornea has a different radius of curvature than the eyeball, the relative motion of the corneal reflection and pupil center by angle and distance, is indicative of the eye line of gaze as the eye views external scene 14. The displacement consists of two parts, a displacement resulting from eyeball rotation relative to light source and a lineal displacement of the center of rotation of the eye normal to the incident light beam. Reference should be had to Young & Sheena's article for a more complete description of the measurement technique than that provided herein.

Eye track camera 30 as well as field-of-view camera 22 are preferably CCD chip cameras to minimize the weight of the system. Alternatively, vidicon tubes with fiber optics as described in the prior art may be used. Also, the eye tracker light illuminator 90 as used in the preferred embodiment is of the conventional near infrared type which produces an unobjectionable, barely visible red spot to the eye of the observer, although, in theory, any light source of any wavelength suitable for tracking may be employed.

Figure 2:
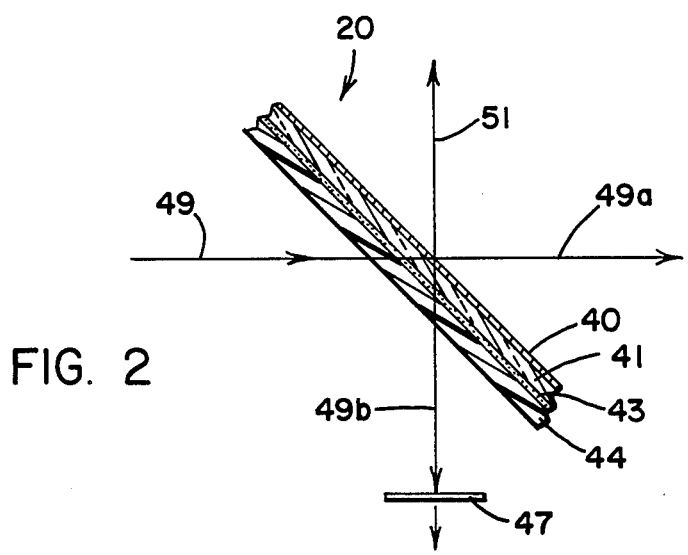
FIGS. 2 and 3 are cross-sectional views illustrating the laminar construction of two different visors which can be used in the system of the present invention.

Referring now to FIG. 2, there is shown the laminar construction of a visor 20 which is suitable for use with a monochromatic (IR) field-of-view camera 22 along with an eye tracker module 24 also using source of illumination 90 at near infrared wavelength. The laminar construction of visor 10 shown in FIG. 2 includes a glass substrate 40 having a front surface facing observer's eye 12 upon which is coated (typically by vacuum deposition) an infrared reflective, "heat mirror" coating which is identical to that used in many of the commerically available "heat mirrors", for example, the Calflex-C heat mirror supplied by the Balzers Optical Group. Secured to the backside of tempered glass substrate 41 by means of a conventional, optically flat glass adhesive 43 is a polycarbonate substrate 44. Polycarbonate sheeting 44 and tempered glass substrate 41 provide impact strength and a safer breakup structure to visor 20. In addition, heat mirror reflective coating 40 is carefully selected and applied to glass substrate 41 so that the coating maximally transmits visible light (at least 95%), maximally reflects near infrared light, does not introduce coloration artifacts and is not critically sensitive to a 45° angle of incidence for optimal performance. Glass substrate 41 on which heat mirror coating 40 is applied is optically flat and thin to minimize distortions and double reflections. The thickness of visor 20 shown in FIG. 2 is only approximately 3 mm. In addition, since field-of-view camera 22 is a CCD chip camera which is maximally sensitive to light and generates a normal black and white image of external scene 14, field-of-view camera 22 is made sensitive only to near infrared light by placing in front of the lens of field-of-view camera 22 an IR-Pass filter 47 so that only infrared or near infrared light is recorded by field-of-view camera 22. Similarly, if eye tracker camera 30 is also a CCD chip camera, a similar IR-Pass filter would be employed. Of course, the retina of observer's eye 12 is not responsive to near infrared light.

As illustrated in FIG. 2, visible light from external scene 14 as shown by arrow 49 is transmitted in a transparent manner through visor 20, as shown by arrow 49a to the observer's eye 12 with minimal reflection distortion and without the introduction of coloration artifacts. Also, that portion of external scene light 49, which is of infrared or near infrared wavelength, is reflected by the back surface of double mirror coating 40, as shown by arrow 49b, and transmitted as a reversed mirror image through IR-Pass filter 47 to the lens of field-of-view camera 22 where the scene is recorded. Additionally, the near infrared light source 90 which is reflected from the front surface of heat mirror coating 44 to observer's eye 12 is similarly reflected off the front surface of heat mirror coating 40 as shown by arrow 51. The construction of visor 20, as shown in FIG. 2, is similar to and may even, in fact, be identical to some "heat mirrors" conventionally manufactured. However, the use of the same visor 20 for both IR eye-tracking and IR scene image (or as explained below, visible light scene image) is believed new and unique and, more specifically, IR eye-tracking and IR scene imaging achieved by reflecting off the front and back surfaces of heat mirror coating 40 different light sources as mirror reversed images in diametrically opposite directions is believed new and unique.

Figure 3:
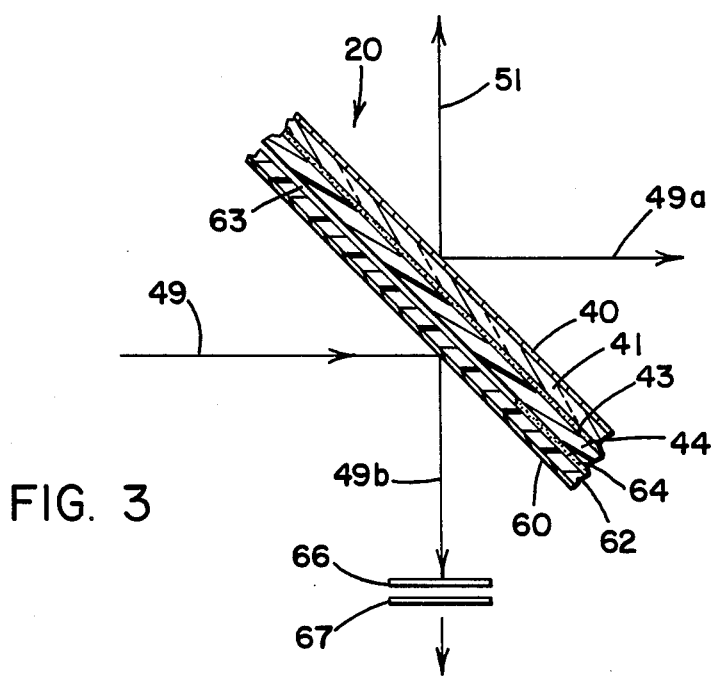

For those applications where it is necessary to use a color camera, or a monochromatic camera using visible light as opposed to infrared light (i.e. a black and white camera) visor 20, as shown in FIG. 2, must be modified as shown in FIG. 3 so that visor 20 reflects not only infrared or near infrared light to eye tracker camera 30, but also reflects the full color visible light to the camera. Visor 20, as shown in FIG. 3, comprises heat mirror coating 40 applied to the front surface of glass substrate 41 and the back surface of glass substrate 41 has a polycarbonate substrate 44 secured thereto by means of adhesive 43 identical to that shown and described for visor 20 of FIG. 2. The modified visor 20 of FIG. 3 additionally has a light-reflecting film or coating 60 applied to one side of a sheet of polarizing film 62 while the opposite side of polarizing film 62 is secured to the back surface of polycarbonate substrate 44. Preferably, polarizing film 62 is removable secured to polycarbonate substrate 44 by means of a pair of spring C-shaped clips 50 (FIG. 1) which merely clamp polarizing film 62 to the visor 20 of FIG. 2 to form the visor 20 of FIG. 3, there being a slight or thin air space 63 between polarizing film 62 and polycarbonate substrate 44. This permits easy construction of visor 20 of FIG. 3. Alternatively, polarizing film 62 could be permanently secured as by adhesive to polycarbonate substrate 44. Polarizing film 62 which is a conventional polarizing sheet is selected to maximally transmit visible light from external scene 14 to the observer's eye 12. As noted, polarizing film 62 is coated with a metallic film 60 so that a portion of the visible light from external scene 14 can be reflected to field-of-view camera 22. The metallic coating could be aluminum vacuum-deposited onto the surface with its thickness carefully controlled so as not to materially impede the transparency of the light from external scene 14 to observer's eye 12. To control haze and other infrared optical artifacts, the lens of field-of-view camera 22 is now fitted with an IR-Cut filter 66 blocking out transmission of excessive infrared light from external scene 14 and eye-tracker optics 24 to field-of-view camera 22 and a polarizing filter 67 to control haze. Polaroid filter 67 is adjusted so as to block the view seen through visor 22. The same considerations of optical flatness, etc., commented on with respect to the visor shown in FIG. 2 apply to visor 20 of FIG. 3 and the thickness of visor 20 in FIG. 3 is controlled to approximately 4.5 mm. The operation of visor 20 in FIG. 3 is similar to that discussed with respect to the visor of FIG. 2. External scene light 49 is, in part, reflected by metallic reflecting coating 60 as shown by arrow 49b to the color field-of-view camera 22 while the remaining portion, which is polarized by film 62, is transmitted as visible light 49a to the observer's eye 12. At the same time, heat mirror coating 40 is reflecting eye tracker light 90 to observer's eye 12 and back as an eye tracker light 51 to eye tracker camera 30.

As thus far defined, the eye-measurement, head-mounted system is functional. With the helmet or head band 26 placed on the observer's head, the field-of-view camera 22 can be activated to project a field-of-view picture and the field-of-view camera 22 and visor 20 geometrical relationship adjusted until the observer indicates that the field-of-view camera picture is what he is actually observing through visor 20. The eye tracker module 24 can then be activated and eye tracker camera 20 adjusted relative visor 20 which is now fixed to generate a point-of-gaze spot appearing on the field-of-view picture an the electronic recording equipment calibrated so that the point-of-gaze spot correlates to that portion of the field-of-view picture or scene which the observer is focusing on. As so used, the optics achieved by visor 20 result in a very stable point-of-gaze spot reflected by eye tracker camera 30 relative to the field-of-view scene as recorded by field-of-view camera 22 and as such is a substantial improvement over prior art systems in terms of both the measurement of the corneal reflection and maintaining the reflected point-of-view spot properly positioned relative to the field-of-view picture.

However, as noted and discussed above, it is in all instances desirable and in fact mandatory in many applications to have field-of-view camera 22 accurately record what is actually seen by observer's eye 12 no matter what the focal distance is of external scene 14. Accordingly, the general arrrangement of the components of the head-mounted system of the present invention permits the system to be adjusted in a manner which compensates for parallax at all focal distances. As best shown in FIG. 1, the distance from eye 12 to visor 20 $D_e$ and the distance from the lens aperture of field-of-view camera 22 to visor 20 $E_c$ are adjusted to be equal to one another. More precisely, eyevisor distance $D_e$ is measured from eye 12 to the pint 71 where eye optic axis 16 is intersected by field-of-view camera's optic axis 70. Eye-camera distance $D_c$ is measured from intersection point 71 to the lens aperture of field-of-view camera 22. Next, the camera angle $C_a$ is made equal to theoptic angle $O_a$. Camera angle $C_a$ is defined as the angle formed between field-of-view camera's optic axis 70 and the back side of visor 20. Eye optic angle $E_1$ is defined as the angle between eye optic axis 16 and the back side of visor 20. It will be appreciated that the angular relationship of field-of-view camera 22, visor 20 and observer's eye 12 could be expressed differently, but the angular relationship thus defined in combination with the defined distances is critical to the operation of the invention in the sense that parallax or perspective errors are eliminated or minimized to result in an external field-of-view scene recorded by field-of-view camera 22 which actually represents what is seen by observer's eye 12. It is also noted the optic axis 72 of eye tracker camera 30 is preferably parallel to optic axis 70 and in this connection, it should be apparent to one skilled in the art that the adjustment mechanism for the helmet or headband could be modified to automatically maintain optic axes 70 and 72 parallel to one another.

In the preferred embodiment and for practical reasons, it has been found that the largest convenient field-of-view has been obtained with the field-of-view camera 22 having a focal length lens of 8 mm. Thus, with the aforementioned distance $E_d$ and $C_d$ set at about 40 mm and the field-of-view camera focal length set at 8 mm, the size of visor 20 is established at approximately 4 inches in height or vertical distance and 7 inches in length in the z-z direction (although the 7 inch length need only be approximately half that distance if the movement of only one eye is being measured). A lens/visor of these specifications will yield a 55° horizontal×45° vertical field-of-view. It has been found empirically that if observer 10 wishes to look beyond this field-of-view there is a high probability that observer 10 will move his head towards the new object of interest rather than exercise the limit of his eye's field-of-view in eyeball rotation. A 55×45° imposed field-of-view is not so wide that the equipment becomes obtrusively bulky and not so small that the eye is usually looking outside that "window". In addition, the adjustment mechanism (described above) permits visor 20 to be positioned in such a manner that the 45° vertical field-of-view can be biased upwards or downwards. For certain application where an eye tends to predominantly look to a higher or lower region of the scene, this adjustment is beneficial.

Figure 4:
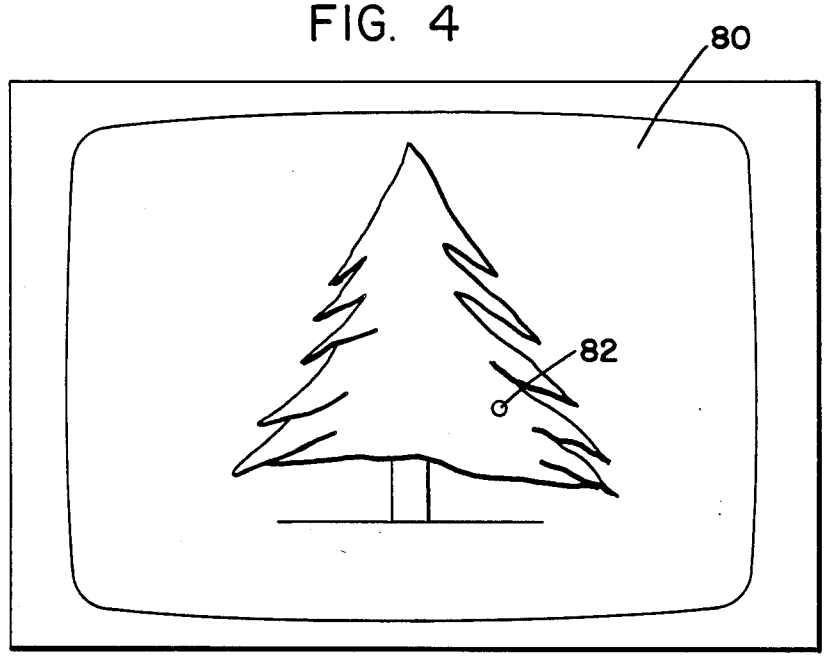
FIG. 4 is a pictorial representation of the point-of-gaze relative to the head of the observer achieved with the present invention.

With visor 20 properly adjusted, conventional circuitry and electronics such as disclosed in ASL's Eye Trac Catalog can be used to accurately monitor a field-of-view scene 80 (FIG. 4) actually seen by observer's eye 12 with a point-of-gaze spot 82 shown on field-of-view scene 80 to obtain position data relative to the head of observer 10. To obtain data on the absolute position of field-of-view picture 80 and point of gaze 82, any conventional head tracker device 85, as shown in FIG. 6 and as discussed above, is applied to helmet or head band 26 of observer 10 to locate the position of the observer's head relative to ground. The output from head tracker device 85, field-of-view camera 22 and eye tracker module 24 can then be inputted to a central control device such as the computer EVM control, diagrammatically indicated at 87, available and described in ASL's catalog. The output from EVM control 87 can then accurately record an absolute point-of-gaze 82 relative to a 360° scan in both horizontal and vertical directions and record such positions through an appropriate position time control 89.

The invention has been described with reference to a preferred embodiment. Obviously, modifications and alterations will become apparent upon a reading and understanding of the specifications. For example, the invention has been described for use with a head mounted system in that the visor, eye tracker and field-of-view camera are all secured to a headband or helmet. This is, in all practicality, where the invention will have the most beneficial application. The relationship, however, between visor, eye-tracker, field-of-view camera and the observer's eye, as taught herein, and in a broader sense the simple use of the visor disclosed herein, could easily occur in an eye measurement system which did not utilize a helmet or headband. For example, the visor, eye-tracker and field-of-view camera could be easily mounted to a floor stand and a chin rest be used for the observer so that the invention can be used in a "remote" eye-measurement system. It is our intention to include all such modifications and alterations insofar as they come within the scope of the invention.

It is thus the essence of the invention to provide a new and improved head-mounted, eye position measurement system which utilizes a unique visor to record an actually observed field-of-view scene while inherently providing improved eye tracker performance.

Having thus defined our invention, we claim:

1. A system for viewing an external scene visually observed through at least one eye of an observer thereof comprising:
    (a) helmet means for mounting on the head of an observer;
    (b) a field-of-view camera mounted on said helmet and having a field-of-view camera axis generally perpendicular to the optic axis of the obserber's eye in the sense that said field-of-view camera's optic axis intersects said eye's optic axis;
    (c) an especially configured visor mounted on said helmet directly in front of said eye, said visor at least partially transparent to light from said scene transmitted to said eye of the observer along said optic axis and reflecting said light from said scene as a mirror image to said field-of-view camera; and
    (d) adjustment means associated with said visor, said field-of-view camera and said helmet means for spacing the visor at equal distances between said eye and said field-of-view camera measured from said intersection of said optic axis, and adjusting the angle between said visor and said field-of-view camera axis, to be equal to the angle between said visor and said eye's optic axis said angles being measured from the same side of said visor so that parallax is minimized to permit the point-of-view camera to accurately record said external scene as visualized by said eye.

2. The system of claim 1 wherein said visor includes an infrared reflective layer for reflecting light of about infrared frequencies along said field-of-view camera's axis, said field-of-view camera being a monochromatic camera sensitive to said reflected light.

3. The system of claim 2 wherein said visor is a glass laminate including a glass substrate having said infrared layer as a coating on one surface thereof reflecting light of about infrared wavelength, a polycarbonate substrate adjacent said glass substrate on the side of said glass substrate opposite said infrared coating, and means to attach said polycarbonate substrate to said glass substrate.

4. The system of claim 3 wherein the thickness of said visor is no more than about 3 mm.

5. The system of claim 4 wherein said visor is sized to yield about a 45 degree vertical × 55 degree horizontal field-of-view.

6. The system of claim 5 wherein said visor has a vertical distance of about 4" and the focal length of the lens of said field-of-view camera is about 8 mm.

7. The system of claim 1 wherein said visor includes a metallic reflecting film on the backside of said visor for reflecting light of visible wavelength along said camera's axis, said camera being a camera capable of recording visible light.

8. The system of claim 7 wherein said visor further includes a polarizing film adjacent said metallic film for transmitting polarized light to the eye of said observer, said camera having a polarized filter adjacent the lens thereof and a filter for preventing light of near infrared wavelength from being transmitted through the lens of said camera.

9. The system of claim 8 wherein said visor is a glass laminate including a glass substrate, an infrared layer applied to the front side of said visor facing the eye of said observer for reflecting light of about infrared wave length, a polycarbonate substrate adhesively secured to the back side of said glass substrate, a polarizing film secured to the back side of said polycarbonate substrate, and said metallic film affixed to the back side of said polarizing film.

10. The system of claim 9 wherein said polarizing film is removably clipped to said glass and polycarbonate substrates.

11. The system of claim 9 wherein said polarizing film is adhesively secured to the back side of said polycarbonate substrate.

12. The system of claim 9 wherein said visor is no more than about 4.5 mm thick.

13. The system of claim 12 wherein said visor is sized to yield about a 45 degree vertical × 55 degree horizontal field-of-view.

14. The system of claim 13 wherein said visor has a vertical distance of about 4" and the focal length of the lens of said field-of-view camera is about 8.0 mm.

15. The system of claim 1 further including eye tracking means for determining the point of gaze of said eye of said observer.

16. The system of claim 15 wherein said eye tracking means includes illuminator means for transmitting a light source at near infrared wavelength frequency in a given direction, an eye monitor camera disposed with its lens axis coaxial with said direction of said light source, said illuminator means reflected by said visor towards the pupil of said eye as a light beam and reflected back as a bright pupil disc and corneal reflection spot beam by said visor to said eye monitor camera whereby the corneal and pupil reflection of the eye of said observer is recorded as a point of gaze spot by said eye monitor camera and means for projecting said point of gaze spot onto said scene as recorded by said point-of-view camera.

17. The system of claim 16 wherein said visor includes an infrared reflective layer for reflecting light of about infrared frequencies along said camera's axis, said camera being a monochromatic camera sensitive to said reflected light.

18. The system of claim 17 wherein said visor is a glass laminate including a glass substrate having said infrared layer as a coating on one surface thereof reflecting light of about infrared wavelength, a polycarbonate substrate adjacent said glass substrate on the side of said glass substrate opposite said infrared coating, and means to attach said polycarbonate substrate to said glass substrate.

19. The system of claim 18 wherein the thickness of said visor is no more than about 3 mm.

20. The system of claim 19 wherein said visor is sized to yield about a 45 degree vertical × 55 degree horizontal field-of-view.

21. The system of claim 20 wherein said visor has a vertical distance of about 4" and the focal length of the lens of said field-of-view camera is about 8 mm.

22. The system of claim 16 wherein said visor includes a metallic reflecting film on the backside of said visor for reflecting light of visible wavelength along said camera's axis, said camera being a camera capable of recording visible light.

23. The system of claim 22 wherein said visor further includes a polarizing film adjacent said metallic film for transmitting polarized light to the eye of said observer, said camera haing a polarized filter adjacent the lens thereof and a filter for preventing light of near infrared wavelength from being transmitted through the lens of said camera.

24. The system of claim 23 wherein said visor is a glass laminate including a glass substrate, an infrared layer applied to the front side of said visor facing the eye of said observer for reflecting light of about infrared wave length, a polycarbonate substrate adhesively secured to the back side of said glass substrate, a polarizing film secured to the back side of said polycarbonate substrate, and said metallic film affixed to the back side of said polarizing film.

25. The system of claim 24 wherein said polarizing film is removably clipped to said glass and polycarbonate substrates.

26. The system of claim 24 wherein said polarizing film is adhesively secured to the back side of said polycarbonate substrate.

27. The system of claim 26 wherein said visor is no more than about 4.5 mm thick.

28. The system of claim 27 wherein said visor is sized to yield about a 45 degree vertical × 55 degree horizontal field-of-view.

29. The system of claim 28 wherein said visor has a vertical distance of about 4" and the focal length of the lens of said field-of-view camera is about 8 mm.

30. A head-mounted eye-movement system for monitoring an observer's view of any external scene as seen through at least one of the observer's eyes, said system comprising:
(a) a field-of-view camera positioned vertically on one side of the optic axis of said eye for recording said scene;
(b) eye tracking means including an eye tracking source of near infrared light for recording the position of said eye as said observer views said scene vertically positioned on the opposite side of the eye's optic axis;
(c) a visor positioned vertically between said field-of-view camera and said eye tracker means at the intersection of said eye's optic axis with said field-of-view camera's optic axis, said visor transparent to visible light to permit said observer to view said scene while looking through said visor;
(d) optical coating means on said visor, said coating means reflecting said eye tracker light to actuate said eye tracking means while reflecting light from said scene to said field-of-view camera to simultaneously permit said field-of-view camera to record said scene.

31. The head-mounted system of claim 30 wherein said eye tracking means includes an eye tracker camera having an optic axis, said eye tracking source of light generally coaxial with said eye tracker camera's optic axis.

32. The head-mounted system of claim 30 further including adjustment means for adjusting the distance between said observer's eye and said visor to be approximately equal to the distance between the aperture of said field-of-view camera lens and said visor, and the angle formed between and by the intersection of said optic axis of said field-of-view camera with said visor being approximately equal to the angle formed between and by the intersection of said optic axis of said observer's eye with said visor, said angles, for reference purposes, measured on the same side of said visor whereby parallax is minimized.

33. The head-mounted system of claim 32 wherein said eye tracking means includes an eye tracker camera having an optic axis, said eye tracking source of light generally coaxial with said eye tracker camera's optic axis.

34. The head-mounted system of claim 33 wherein said eye tracker camera's optic axis is approximately parallel to said field-of-view camera's optic axis.

35. The head-mounted system of claim 32 wherein said field-of-view camera has an 8 mm focal length lens.

36. The head-mounted system of claim 35 wherein said eye tracker means is reflective to track the movement of said eye over a 55 degree horizontal and 45 degree vertical field-of-view.

37. The head-mounted system of claim 36 wherein said eye tracking means includes an eye tracker camera having an optic axis, said eye tracking source of light generally coaxial with said eye tracker camera's optic axis.

38. The head-mounted system of claim 37 wherein said eye tracker camera's optic axis is approximately parallel to said field-of-view camera's optic axis.

39. The head-mounted system of claim 30 wherein said optical coating means includes an infrared optical coating for reflecting light having near infrared wavelength, said infrared optical coating reflecting said infrared source light on one side thereof for actuating said eye tracking means while reflecting scene light of near infrared wavelength to said field-of-view camera for recording said scene, said field-of-view camera being a monochromatic infrared camera.

40. The head-mounted system of claim 39 further including adjustment means for adjusting the distance between said observer's eye and said visor to be approximately equal to the distance between the aperture of said field-of-view camera lens and said visor, and the angle formed between and by the intersection of said optic axis of said field-of-view camera with said visor being approximately equal to the angle formed between and by the intersection of said optic axis of said observer's eye with said visor, said angles, for reference purposes, measured on the same side of said visor whereby parallax is minimized.

41. The head-mounted system of claim 40 wherein said eye tracking means includes an eye tracker camera having an optic axis, said eye tracking source of light generally coaxial with said eye tracker camera's optic axis.

42. The head-mounted system of claim 41 wherein said eye tracker camera's optic axis is approximately parallel to said field-of-view camera's optic axis.

43. The head-mounted system of claim 30 wherein said optical coating means includes an infrared optical coating for reflecting light having near infrared wavelength on one side of said visor for actuating said eye tracking means and a visible light optical coating on the opposite side of said visor for reflecting scene light of visible wavelength to said point-of-view camera, said point-of-view camera being a camera capable of recording a visible light.

44. The head-mounted system of claim 43 wherein said visor has a polarizing film adjacent said visible light optical coating for polarizing said scene light, and said field-of-view camera having a polarizing filter lens and an infrared cut filter lens preventing transmission of light having near infrared wavelength to said field-of-view camera.

45. The head-mounted system of claim 44 further including adjustment means for adjusting the distance betweem said observer's eye and said visor to be approximately equal to the distance between the aperture of said field-of-view camera lens and said visor, and the angle formed between and by the intersection of said optic axis of said field-of-view camera with said visor being approximately equal to the angle formed between and by the intersection of said optic axis of said observer's eye with said visor, said angles, for reference purposes, measured on the same side of said visor whereby parallax is minimized.

46. The head-mounted system of claim 45 wherein said eye tracking means includes an eye tracker camera having an optic axis, said eye tracking source of light generally coaxial with said eye tracker camera's optic axis.

47. The head-mounted system of claim 46 wherein said eye tracker camera's optic axis is approximately parallel to said field-of-view camera's optic axis.

48. The head-mounted system of claim 47 further including head position means for sensing the position of the head of said observer and means for combining data from said eye-tracker camera, said field-of-veiw camera and said head position means to determine said observer's absolute point-of-gaze.

49. In a head-mounted eye monitor system including an eye tracker camera, an external eye tracker source of near infrared light, and a field-of-view camera for recording the external scene viewed by at least one eye of the observer, the improvement comprising:
  (a) means for mounting at least the lens of said eye tracker camera, in fixed relationship to the head of the observer, vertically spaced from and on one side of the optic axis of said observer's eye;
  (b) means for mounting at least the lens of said field-of-view camera in fixed relationship to the head of the observer vertically spaced from and on the opposite side of the optic axis of said observer's eye from that of said eye tracker camera;
  (c) a visor positioned at the intersection of the optic axis of said observer's eye with the optic axis of said field-of-view camera and transparent to visible light from said external scene; and
  (d) reflective means on said visor for reflecting said eye tracker light from one side of said visor to said eye tracker camera for recording the positions of said observer's eye and reflecting light from said external scene from the opposite side of said visor and in the opposite direction to said field-of-view camera for recording said external scene as viewed by said observer's eye.

50. The system of claim 49 further including adjustment means for adjusting the distance between said observer's eye and said visor to be approximately equal to the distance between the aperture of said field-of-view camera lens and said visor, and for adjusting the angle formed between and by the intersection of said optic axis of said field-of-view camera with said visor to be approximately equal to the angle formed between and by the intersection of said optic axis of said observer's eye with said visor, said angles, for reference purposes, measured on the same side of said visor whereby parallax is minimized.

51. The head-mounted system of claim 50 wherein said eye tracking means includes an eye tracker camera having an optic axis, said eye tracking source of light generally coaxial with said eye tracker camera's optic axis.

52. The head-mounted system of claim 51 wherein said eye tracker camera's optic axis is approximately parallel to said field-of-view camera's optic axis.

53. The head-mounted system of claim 52 wherein said optical coating means includes an infrared optical coating for reflecting light having near infrared wavelength, said infrared optical coating reflecting said infrared source light on one side thereof for actuating said eye tracking means while reflecting scene light or near infrared wavelength to said field-of-view camera for recording said scene, said field-of-view camera being a monochromatic infrared camera.

54. The head-mounted system of claim 52 wherein said optical coating means includes an infrared optical coating for reflecting light having near infrared wavelength on one side of said visor for actuating said eye tracking means and a visible light optical coating on the opposite side of said visor for reflecting scene light of visible wavelength to said point-of-view camera, said point-of-view camera being a camera capable of recording a visible light.

55. The head-mounted system of claim 54 wherein aid visor has a polarizing film adjacent said visible light optical coating for polarizing said scene light, and said field-of-view camera having a polarizing filter lens and an infrared cut filter lens preventing transmission of light having near infrared wavelength to said field-of-view camera.

56. An eye-movement monitoring system comprising an eye-tracker camera,
  an external eye-tracker source of near infrared light,
  a field-of-view camera for recording the external scene viewed by at least one eye of an observer,
  means for mounting at least the lens of said eye-tracker camera, vertically spaced from and on one side of the optic axis of said observer's eye;
  means for mounting at least the lens of said field-of-view camera vertically spaced from and on the opposite side of the optic axis of said observer's eye from that of said eye-tracker camera;

a visor positioned at the intersection of the optic axis of said observer's eye with the optic axis of said field-of-view camera and transparent to visible light from said external scene; and reflective means on said visor for reflecting said eyetracker light from one side of said visor to said eyetracker camera for recording the positions of said observer's eye and reflecting light from said external scene from the opposite side of said visor and in the opposite direction to said field-of-view camera for recording said external scene as viewed by said observer's eye.

57. The eye-movement monitoring system of claim 56 wherein said means for mounting includes a mounting affixed to the head of said observer.

* * * * *